(12) United States Patent
Giladi et al.

(10) Patent No.: US 12,377,265 B2
(45) Date of Patent: Aug. 5, 2025

(54) NONCONDUCTIVE FIELD GUIDE FOR RESECTION CAVITY, AND SYSTEMS AND METHODS OF USING SAME

(71) Applicant: NOVOCURE GMBH, Baar (CH)

(72) Inventors: Moshe Giladi, Haifa (IL); Lilach Avigdor, Haifa (IL); Ariel Naveh, Haifa (IL)

(73) Assignee: NOVOCURE GMBH, Baar (CH)

( * ) Notice: Subject to any disclaimer, the term of this patent is extended or adjusted under 35 U.S.C. 154(b) by 291 days.

(21) Appl. No.: 17/854,323

(22) Filed: Jun. 30, 2022

(65) Prior Publication Data

US 2023/0001195 A1 Jan. 5, 2023

Related U.S. Application Data

(60) Provisional application No. 63/216,970, filed on Jun. 30, 2021.

(51) Int. Cl.
*A61N 1/36* (2006.01)
*A61L 27/26* (2006.01)
*A61L 27/54* (2006.01)
*A61M 31/00* (2006.01)
*A61N 1/05* (2006.01)
*B33Y 80/00* (2015.01)

(52) U.S. Cl.
CPC .......... *A61N 1/36002* (2017.08); *A61L 27/26* (2013.01); *A61L 27/54* (2013.01); *A61M 31/002* (2013.01); *A61L 2300/404* (2013.01); *A61M 2205/054* (2013.01); *A61N 1/0529* (2013.01); *B33Y 80/00* (2014.12)

(58) Field of Classification Search
None
See application file for complete search history.

(56) References Cited

U.S. PATENT DOCUMENTS

| | | | | |
|---|---|---|---|---|
| 6,969,604 B1 * | 11/2005 | Yakovenko | ............ | C12M 35/02 435/288.1 |
| 2005/0209642 A1 * | 9/2005 | Palti | ....................... | A61N 1/326 607/2 |
| 2007/0239213 A1 * | 10/2007 | Palti | ......................... | A61N 1/40 607/2 |
| 2015/0272669 A1 | 10/2015 | Brucker | | |

(Continued)

OTHER PUBLICATIONS

Kevin Sheets, et al. Image-Guided Resection of Glioblastoma and Intracranial Implantation of Therapeutic Stem Cell-seeded Scaffolds. J Vis Exp. Jul. 16, 2018;(137):57452. doi: 10.3791/57452. PMID: 30059037; PMCID: PMC6126468. (Year: 2018).*

(Continued)

*Primary Examiner* — James M Kish
*Assistant Examiner* — James Moss
(74) *Attorney, Agent, or Firm* — Ballard Spahr LLP (57) ABSTRACT

A method for treating tumor cells around a resection cavity comprises positioning a nonconductive material within a resection cavity that is adjacent to a target region. At least a first electrode and a second electrode are positioned relative to the tumor resection cavity so that electric fields between the at least one first electrode and the at least one second electrode travel through the target region. Tumor-treating electric fields are the generated between the at least one first electrode and the at least one second electrode.

16 Claims, 9 Drawing Sheets

(56) References Cited

U.S. PATENT DOCUMENTS

2020/0114141 A1\* 4/2020 Bomzon ................. A61N 1/08
2021/0138233 A1   5/2021 Deslauriers
2021/0162228 A1   6/2021 Uyman et al.

OTHER PUBLICATIONS

Search Report and Written Opinion of corresponding PCT Application No. PCT/IB2022/05619.

\* cited by examiner

NONCONDUCTIVE FIELD GUIDE FOR RESECTION CAVITY, AND SYSTEMS AND METHODS OF USING SAME

CROSS-REFERENCE TO RELATED APPLICATION

This application claims priority to and the benefit of the filing date of U.S. Provisional Patent Application No. 63/216,970, filed Jun. 30, 2021, which is incorporated herein by reference in its entirety.

BACKGROUND

A tumor can be treated by resection to remove all or a portion of the tumor, thereby leaving a resection cavity. Often, when doing so, not all of the tumor cells are extracted. For example, for brain tumors, such as glioblastoma, a bulk of the tumor can be removed, but portions (often, finger-like roots) of the tumor can be interlaced with healthy cells. Thus, peripheral tumor cells cannot be resected without also removing or destroying a substantial quantity of healthy cells, which can be undesirable.

Accordingly, after resection of the bulk of the tumor, a secondary treatment process can treat the remaining cells surrounding the resection cavity (e.g., within the peritumoral region). One such treatment includes tumor-treating electrical fields (TTFields). However, upon resection of the bulk of the tumor, the cavity is backfilled with fluid that is highly electrically conductive. Accordingly, a substantial portion of the TTFields pass directly through the fluid within the cavity, thereby reducing efficacy of the TTFields in treating the tumor cells surrounding the cavity.

SUMMARY

Described herein, in various aspects, is a method that comprises positioning a nonconductive material within a resection cavity that is adjacent to a target region. At least one first electrode and at least one second electrode can be positioned relative to the tumor resection cavity so that electric fields between the at least one first electrode and the at least one second electrode travel through the target region. Tumor-treating electric fields can be generated between the at least one first electrode and the at least one second electrode.

In another aspect, a system can comprise at least one first electrode, at least one second electrode, and a nonconductive material positioned between the at least one first electrode and the at least one second electrode. A signal generator can be in electrical communication with each one of the at least one first electrode and the at least one second electrode. The signal generator can be configured to generate electric fields between the at least one first electrode and the at least one second electrode.

In another aspect, a nonconductive, biocompatible material can be configured for receipt into a resection cavity. The nonconductive material can define an inner passageway that is configured to fill with fluid to conduct electric fields therethrough.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "an electrode" can refer to one or more of such electrodes, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects. Similarly, if further aspects, when values are approximated by use of "approximately," "substantially," and "generally," it is contemplated that values within up to 15%, up to 10%, up to 5%, or up to 1% (above or below) of the particularly stated value can be included within the scope of those aspects.

Except where otherwise indicated, the word "or" as used herein can mean any one member of a particular list and, in other optional aspects, can include any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Figure 7:
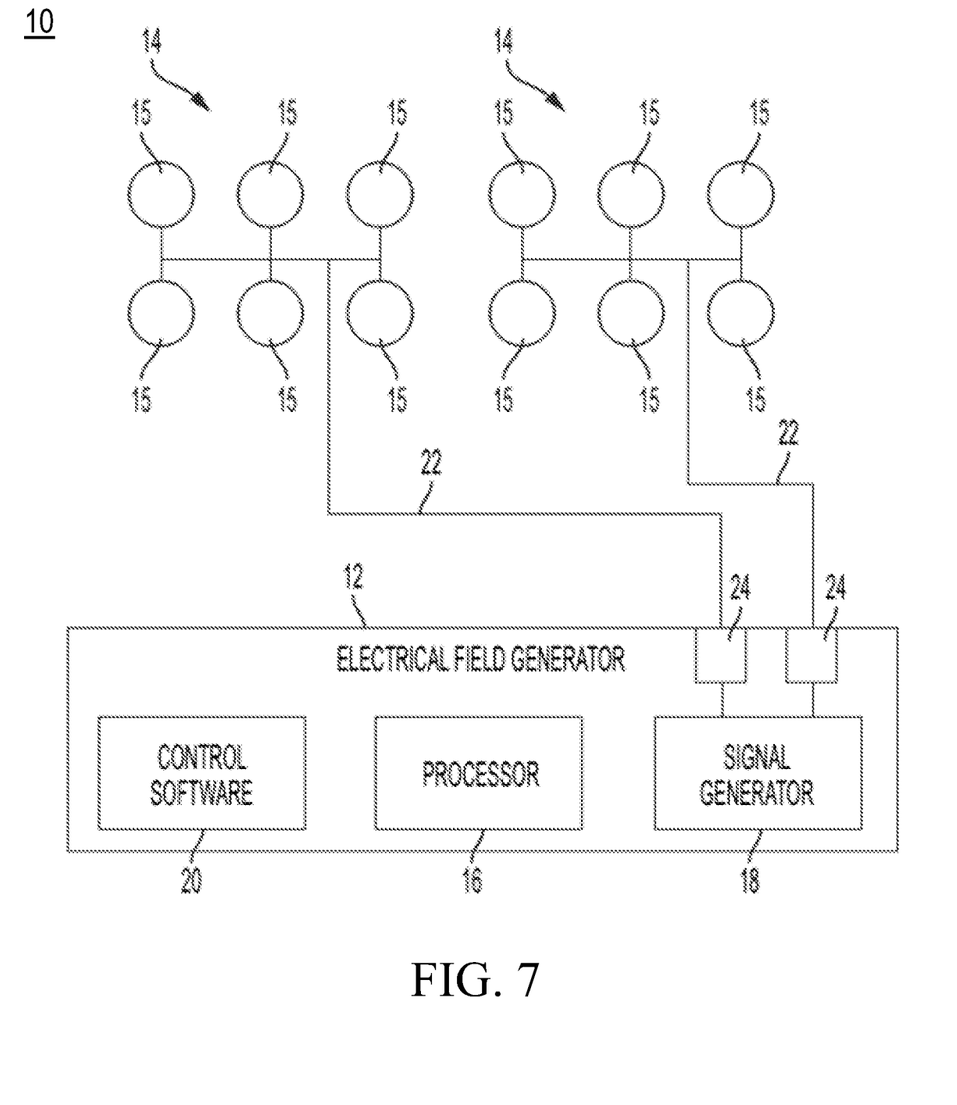
FIG. 7 is a schematic diagram of a treatment system as disclosed herein.

FIG. 7 shows an example apparatus 10 for electrotherapeutic treatment as disclosed herein. Generally, the apparatus 10 may be a portable, battery or power supply operated device that produces alternating electrical fields within the body by means of stimulation zones as disclosed herein (e.g., transducer arrays or electrodes). The apparatus 10 may comprise an electrical field generator 12 and one or more stimulation zones (shown in this exemplary configuration as transducer arrays 14). The apparatus 10 may be configured to generate tumor treating fields (TTFields) (e.g., at 150 kHz) via the electrical field generator 12 and deliver the TTFields to an area of the body through the stimulation zones (e.g., one or more transducer arrays 14 or electrodes). The electrical field generator 12 may be powered by a battery and/or power supply.

As shown in FIG. 7, each transducer array 14 can comprise a plurality of electrodes or transducers 15. As used herein, features described with respect to electrodes are also applicable to transducers, and vice versa, unless otherwise indicated. Accordingly, the terms electrode and transducer are used interchangeably herein. In exemplary aspects, the transducers 15 can capacitively couple an AC signal into a subject's body. In further aspects, the transducers 15 can comprise a layer of conductive material, such as a layer of at least one metal (e.g., stainless steel, gold, and/or copper). Additionally, or alternatively, it is contemplated that the transducers 15 can comprise one or more layers of conductive adhesive (e.g., hydrogel). Exemplary transducers 15 can further comprise dielectric material. Optionally, the transducers 15 can comprise ceramic discs, such as described in U.S. Pat. No. 8,715,203, which is incorporated herein by reference. In additional or alternative aspects, it is contemplated that the transducers 15 can comprise polymer insulating layers and/or other insulating material.

The electrical field generator 12 may comprise a processor 16 in communication with a signal generator 18. The electrical field generator 12 may comprise control software 20 configured for controlling the performance of the processor 16 and the signal generator 18.

The signal generator 18 may generate one or more electric signals in the shape of waveforms or trains of pulses. The signal generator 18 may be configured to generate an alternating voltage waveform at frequencies in the range from about 50 KHz to about 1 MHz (preferably from about 50 KHz to about 500 KHz or from about 100 KHz to about 300 KHz) (e.g., the TTFields). The voltages are such that the electrical field intensity in tissue to be treated is typically in the range of about 0.1 V/cm to about 10 V/cm.

One or more outputs 24 of the electrical field generator 12 may be coupled to one or more conductive leads 22 that are attached at one end thereof to the signal generator 18. The opposite ends of the conductive leads 22 are connected to the one or more stimulation zones (e.g., transducer arrays 14) that are activated by the electric signals (e.g., waveforms). The conductive leads 22 may comprise standard isolated conductors with a flexible metal shield and may be grounded to prevent the spread of the electrical field generated by the conductive leads 22. The one or more outputs 24 may be operated sequentially. Output parameters of the signal generator 18 may comprise, for example, an intensity of the field, a frequency of the waves (e.g., treatment frequency), and a maximum allowable temperature of the one or more stimulation zones (e.g., transducer arrays 14). The output parameters may be set and/or determined by the control software 20 in conjunction with the processor 106. After determining a desired (e.g., optimal) treatment frequency, the control software 20 may cause the processor 16 to send a control signal to the signal generator 18 that causes the signal generator 18 to output the desired treatment frequency to the one or more stimulation zones (e.g., transducer arrays 14). Similarly, it is contemplated that the processor 16 can be in communication with a temperature sensor (e.g., a thermistor or thermocouple) that is configured to measure temperature at a respective transducer array, and when a temperature threshold is reached, the control software 20 can cause the processor 16 to decrease a frequency and/or intensity of the electric signal provided by the signal generator. In further aspects, it is contemplated that the processor 16 can be in communication with a sensor that is configured to measure an intensity of the electric field generated by the apparatus 10, and the control software 20 can cause the processor 16 to decrease or increase a frequency and/or intensity of the electric signal to achieve a desired decrease or increase in the field intensity.

The one or more stimulation zones (e.g., transducer arrays 14) may be configured in a variety of shapes and positions so as to generate an electrical field of the desired configuration, direction and intensity at a target volume so as to focus treatment. Optionally, the one or more stimulation zones (e.g., transducer arrays 14) may be configured to deliver two perpendicular field directions through the volume of interest (e.g., a target region).

Figure 1:
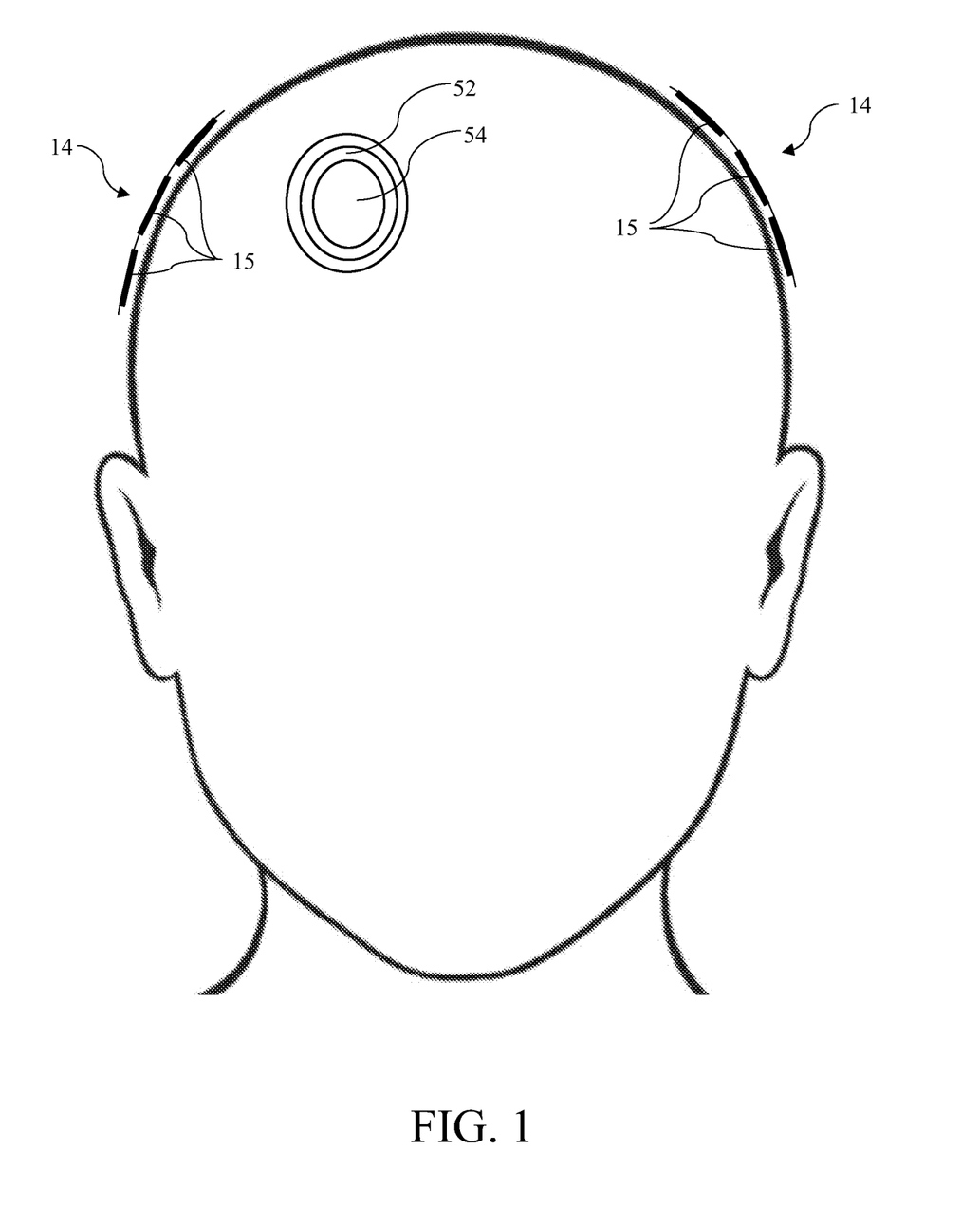
FIG. 1 is a schematic diagram of a treatment system as disclosed herein positioned on a patient.
Figure 2:
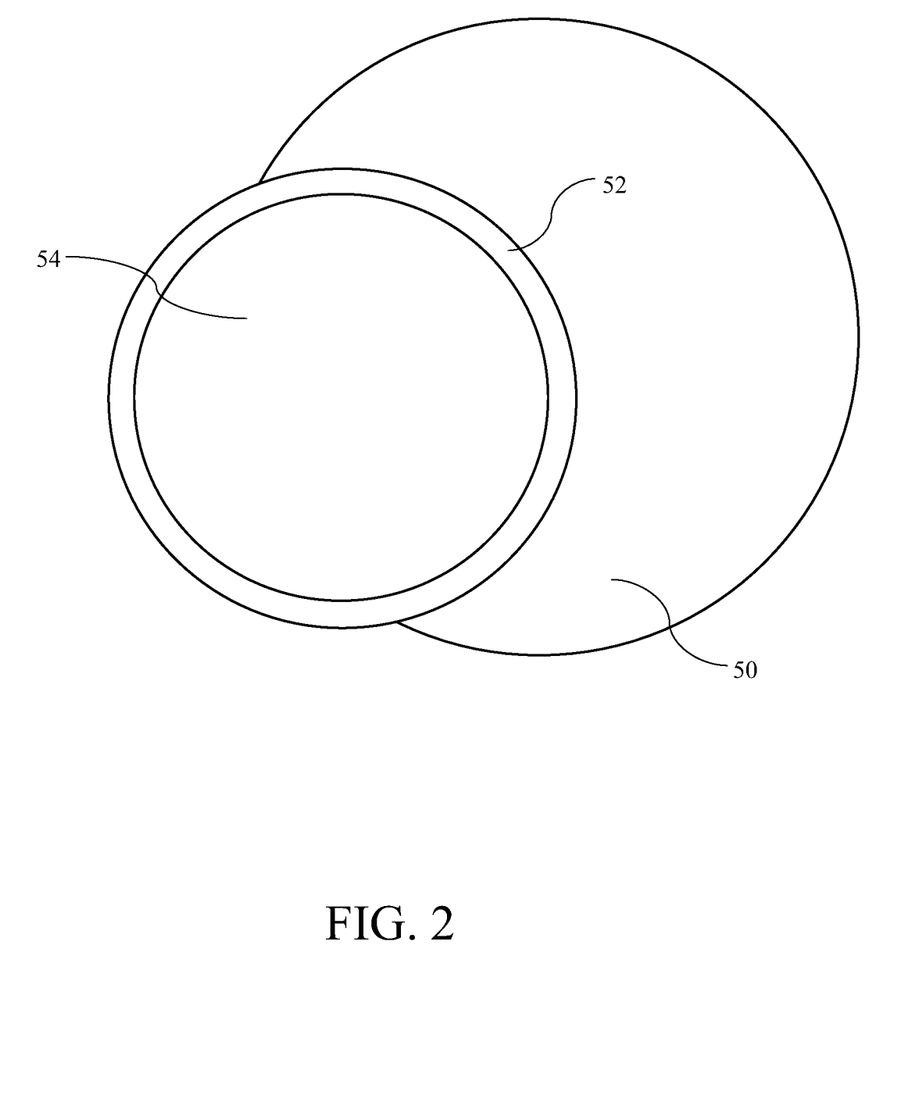
FIG. 2 is a schematic diagram of a tumor, resection cavity, and nonconductive material as disclosed herein.
Figure 3A:
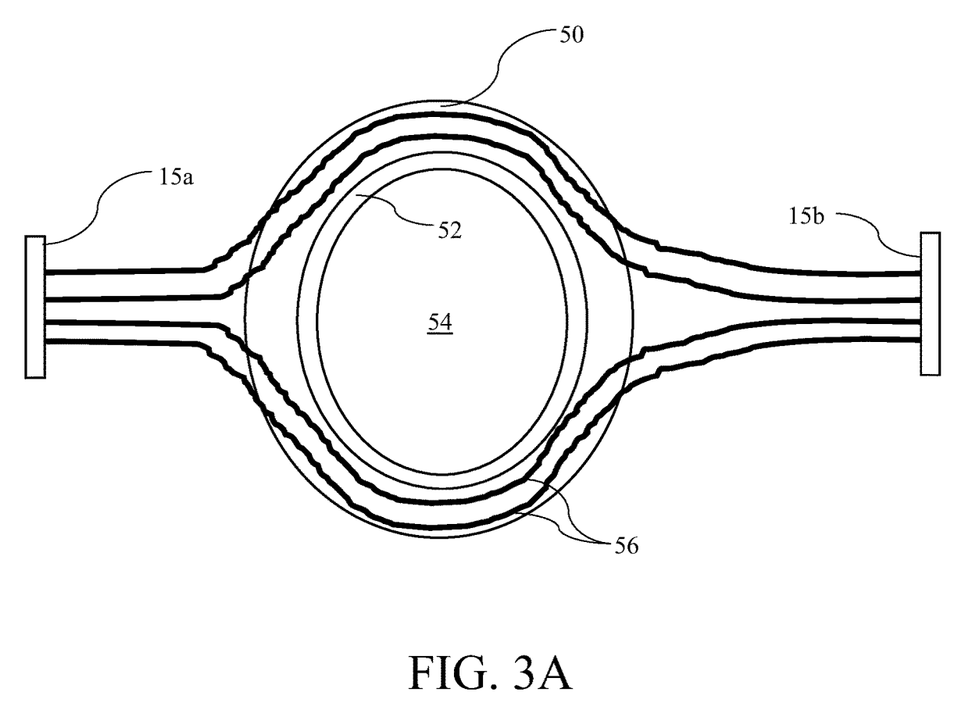
FIG. 3A is a schematic diagram of electric field lines traveling between electrodes/transducers and around a nonconductive material, as disclosed herein.
Figure 3B:
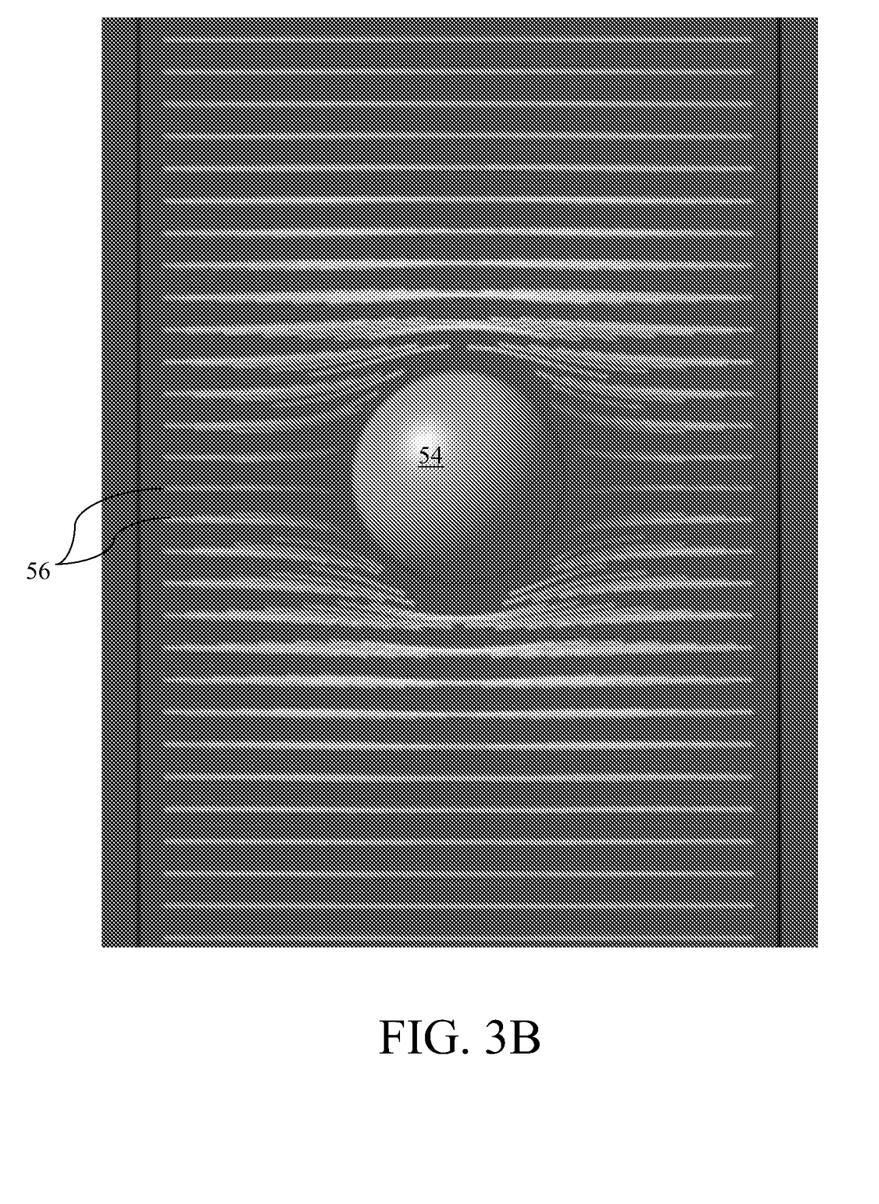
FIG. 3B is a model showing electric field lines around the nonconductive material.
Figure 5:
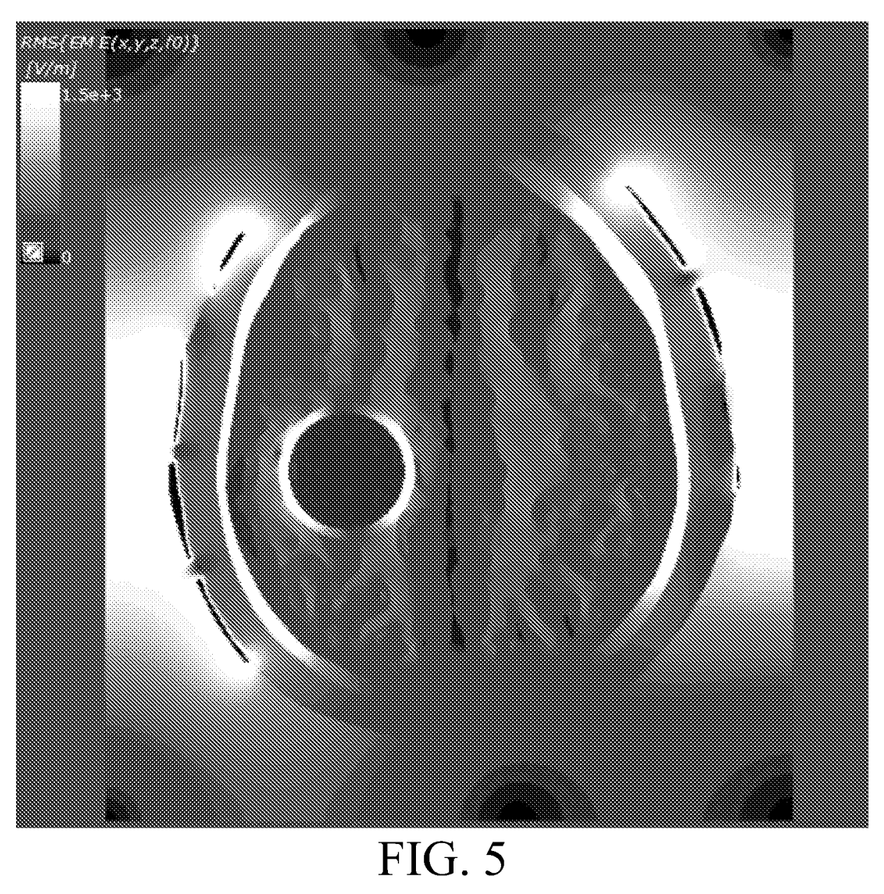
FIG. 5 is a model of electric field distribution through a brain with a nonconductive material disposed therein.
Figure 6:
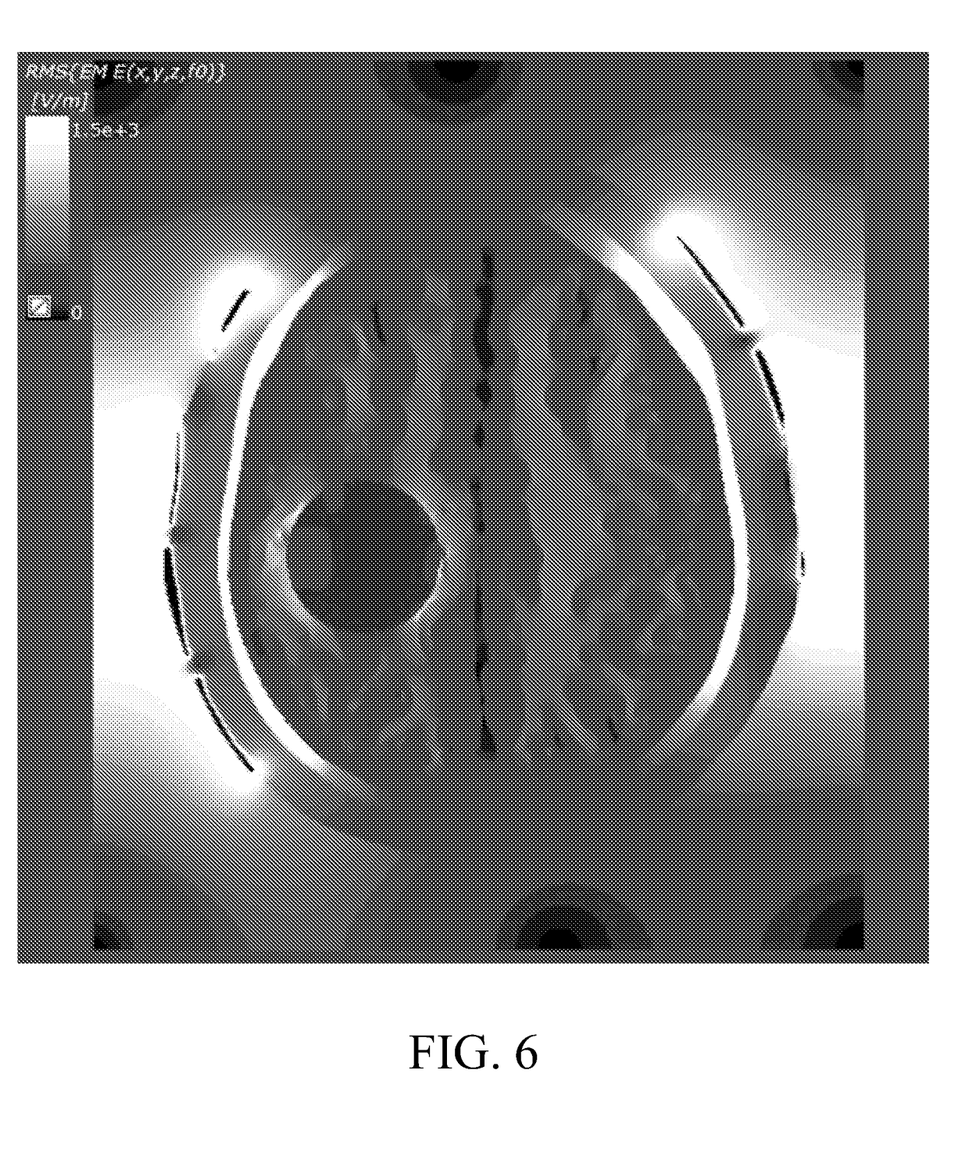
FIG. 6 is a model of electric field distribution through a brain without nonconductive material disposed therein.

Referring to FIGS. 1-2, a target region 50 can be a region adjacent to (optionally, surrounding) a resection cavity 52. That is, at least a portion of a tumor can be resected (e.g., in a resection surgery or other surgical procedure) to form the resection cavity 52. A nonconductive material 54 can be positioned within the resection cavity 52. As used herein, the term "nonconductive material" refers to a material that is not electrically conductive and that does not conduct electric fields. Optionally, the nonconductive material 54 can be implanted in the resection cavity 52 during the surgery in which the resection is performed. In further aspects, the nonconductive material 54 can be implanted in a subsequent surgery (separate from and following the surgery in which the resection is performed). In further aspects, the nonconductive material 54 can be injected into the resection cavity 52 or inserted through a port or stent that provides access to the resection cavity. At least one first electrode 15*a* and at least one second electrode 15*b* can be positioned relative to the resection cavity 52 so that electric fields between the at least one first electrode and the at least one second electrode travel through the target region 50. For example, as shown in FIG. 3A, in some optional aspects, the first electrode 15*a* and second electrode 15*b* can be positioned with the resection cavity 52 therebetween. Using the electric field generator 12, tumor-treating electric fields 56 can be generated between the at least one first electrode 15*a* and the at least one second electrode 15*b*. Referring to FIGS. 3A and 3B, the nonconductive material 54 can cause the electric fields 56 to circumvent (avoid passing through), generally circumvent, or at least partially circumvent the resection cavity. Moreover, the nonconductive material 54 can displace volume that is typically filled with conductive fluid (e.g., cerebrospinal fluid (CSF)), thereby eliminating a low-resistance pathway that is conventionally available to the electric fields when the nonconductive material is not present. Accordingly, use of the nonconductive material 54 can increase the concentration of tumor-treating fields passing through the target region 50, thereby improving efficacy of the treatment. For example, as shown in the models of FIGS. 5 and 6, the nonconductive material 54 can increase the concentration of electric fields surrounding the nonconductive material, indicated by the lighter area surrounding the dark circle in FIG. 5 relative to the area surrounding the dark circle in FIG. 6.

In various aspects, the nonconductive material 54 can be biocompatible. In some optional aspects, the nonconductive material 54 can comprise, or be embodied as, a scaffold, a hydrogel, a film, or a three-dimensionally (3D) printed construct.

In aspects in which the nonconductive material 54 is a 3D printed construct, the nonconductive material can comprise one of a hydrogel or a polyimide.

In aspects in which the nonconductive material 54 is a scaffold, the scaffold can optionally be a nanofibrous scaffold or a hybrid scaffold. In some aspects, the scaffold can optionally comprise natural polymer. For example, the scaffold can comprise one or more of hyaluronic acid, fibrin, chitosan, gelatin, agarose, collagen, or combinations thereof. In further aspects, scaffold can comprise synthetic polymer. For example, the scaffold can comprise one or more of Polyethylene Glycol (PEG), polypropylene fumarate (PPF), polyanhydride, polycaprolactone (PCL), polyphosphazene, polyether ether ketone (PEEK), polylactic acid (PLA), poly (glycolic acid) (PGA), or combinations thereof.

In some aspects, the scaffold can be a three-dimensional (3D) bi-layer scaffold. Said three-dimensional (3D) bi-layer scaffold can optionally comprise biological decellularized human amniotic membrane (AM) with viscoelastic electrospun nanofibrous silk fibroin (ESF).

In some aspects, the nonconductive material comprises a biosheet (e.g., optionally, a silicone biosheet). The biosheet can optionally be a thin structure that covers at least a portion of a surface defining the resection cavity. Thus, in some optional aspects, the biosheet can define and/or surround an inner volume. Optionally, the inner volume of the biosheet can receive and fill with fluid from the body. Optionally, the biosheet can comprise a mesh. In some optional aspects, the biosheet can solidify once implanted. In use, prior to solidifying, it is contemplated that the shape of the biosheet can be selectively adjusted to match or complement a shape of at least a portion of a resection cavity.

In some optional aspects, the nonconductive material can comprise a chemotherapy agent that is configured to be released into the target region 50. For example, the chemotherapy agent can comprise, for example, a taxane such as paclitaxel (I), docetaxel (II), cabazitaxel (III), and any other taxane or taxane derivatives, non-limiting examples of which are taxol B (cephalomannine), taxol C, taxol D, taxol E, taxol F, taxol G, taxadiene, baccatin III, 10-deacetylbaccatin, taxchinin A, brevifoliol, and taxuspine D, and also include pharmaceutically acceptable salts of taxanes. In further aspects, the nonconductive material can comprise a nanogel. The nanogel can have one or more chemotherapy agents that are configured for slow release. For example DNA nanogels can be comprise structures that biomarker FEN1 can recognize and cut. Some exemplary nanogels for providing chemotherapy are provided in American Chemical Society. "A DNA-based nanogel for targeted chemotherapy." ScienceDaily. ScienceDaily, 18 Nov. 2020. www-.sciencedaily.com/releases/2020/11/201118141731.htm, which is hereby incorporated by reference herein in its entirety. Further exemplary nanogels for delivering chemotherapy are provided in Niu, Kai, et al. "Polypeptide nanogels with different functional cores promote chemotherapy of lung carcinoma." Frontiers in pharmacology 10 (2019): 37, which is hereby incorporated by reference herein in its entirety.

In some optional aspects, the nonconductive material can comprise an antibacterial agent. In this way, the nonconductive material can serve the additional purpose of inhibiting infection. Exemplary antibacterial agents include, for example and without limitation, macrolides, clindamycin, and doxycycline. In some optional aspects, a nanogel can be used to deliver one or more antibacterial agents, as described for example, in Sahu, Prashant, et al. "Nanogels: a new dawn in antimicrobial chemotherapy." Antimicrobial Nanoarchitectonics. Elsevier, 2017. 101-137, which is hereby incorporated by reference herein in its entirety.

Optionally, the nonconductive material can be configured to break down and be absorbed by the body (i.e., be bioabsorbable). In further aspects, the nonconductive material can be configured not to break down. Optionally, the nonconductive material 54 can be removed after treatment such that the nonconductive material 54 functions as a temporary insert. For example, a stent or port can provide access to the nonconductive material 54 to permit removal of the nonconductive material after a desired amount (e.g., duration) of treatment with the nonconductive material. In this example, it is contemplated that a stent or port can extend through or be in fluid communication with an opening through a portion of the body of a patient (e.g., a hole formed through the cranium of the patient, or an access port formed in the torso (e.g., abdomen or back) of the patient). In further aspects, the nonconductive material can be left within the patient indefinitely (or until such time as the nonconductive material is absorbed by the body).

In some optional aspects, the nonconductive material 54 can comprise an oil. Accordingly, in some optional aspects, the nonconductive material 54 can be a fluid that fills, and conforms to the shape of, at least a portion of the resection cavity 52. As further described herein, in further optional aspects, the nonconductive material 54 can compose both a rigid material and a fluid material.

Accordingly, in some optional aspects, the nonconductive material 54 can have a defined structure and geometry. For example, optionally, the nonconductive material can be shaped to be complementary to the geometry of the resection cavity. Optionally, the nonconductive material can be spherical. In further aspects, the nonconductive material can be oblong, cylindrical, polyhedral, irregularly shaped, or amorphous. In still further aspects, other shapes are contemplated depending on patient anatomy and geometry of the resection cavity. Optionally, the nonconductive material 54 can support the matter surrounding the resection cavity to inhibit collapse thereof. In further aspects, the nonconductive material can have a structure that is configured to conform to the shape of the resection cavity. In yet further aspects, the nonconductive material 54 can comprise both a portion having a defined structure and a fluid that is configured to conform to the shape of the resection cavity.

Figure 4:
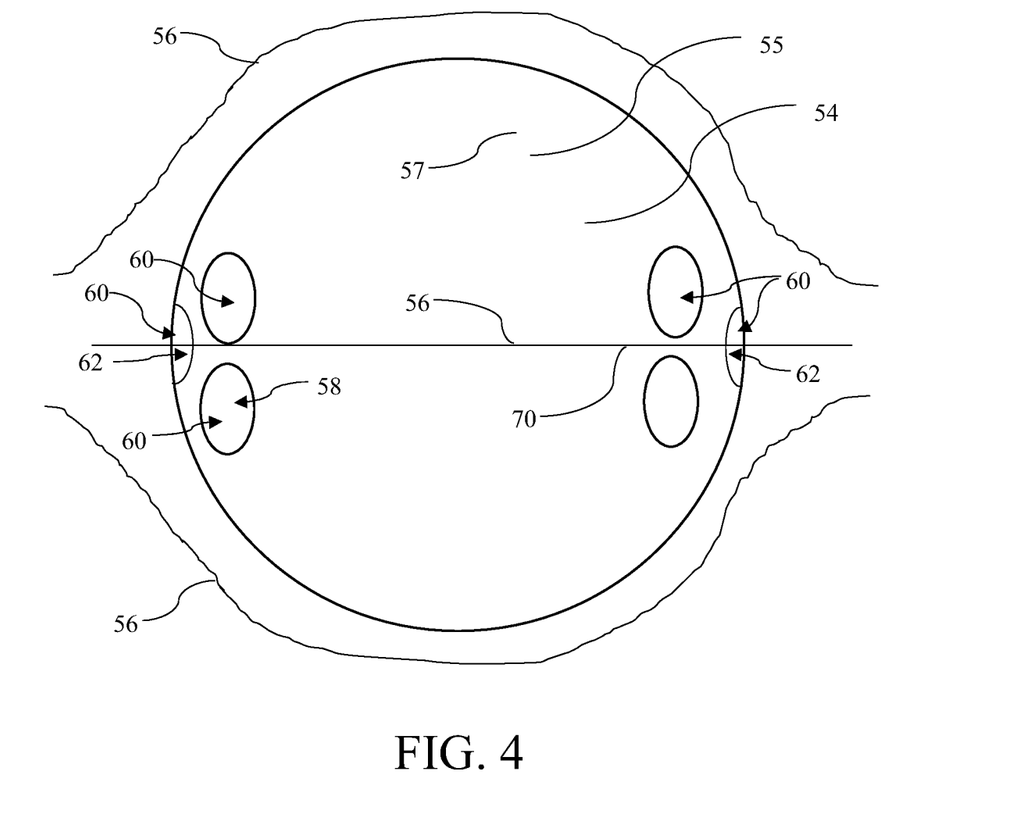
FIG. 4 is a schematic diagram of an exemplary nonconductive material as disclosed herein.

Depending on the size, shape, and location of the target region 50 and the resection cavity 52, in some (but not all) situations a nonconductive material 54 forming a complete electric field barrier therethrough can lead to a sub-optimal distribution of electric field throughout the entire target region. Accordingly, referring also to FIG. 4, in some optional aspects, the nonconductive material 54 can be embodied as a nonconductive body 55 comprising a biocompatible material. The nonconductive body 55 can define at least one pathway therethrough for electric fields to travel. For example, in some aspects, the nonconductive body 55 can be hollow, defining an outer surface 57 and an interior volume 58 (e.g., a shell having a thickness of less than 1 mm, about 1 mm, at least 1 mm, at least 2 mm, at least 3 mm, no more than 5 mm, or greater than 5 mm). The nonconductive body 55 can further comprise a plurality of openings 60 between (or otherwise in fluid communication with) the outer surface 57 and the interior volume 58. In these aspects, it is contemplated that the inner volume 58 can fill with fluid (e.g., CSF) so that the nonconductive body 55 defines an inner passageway 62 between at least two openings of the plurality of openings 60, which can optionally be positioned on opposing sides of the nonconductive body. Said inner passageway 62 can conduct electric fields therethrough. Moreover, the inner passageway 62 can cause fields to converge and concentrate within the resection cavity while also maintaining an effective field strength throughout the target region. Accordingly, as shown in FIG. 4, a portion 70 of the electric fields 56 can enter through openings 60 on one side of the nonconductive body 55 and exit through openings on the other (optionally, opposed) side of the nonconductive body. For example, it is contemplated that a first plurality of openings (for example, two, three, four, or more openings) can be positioned on a first side of the nonconductive body 55, and a second plurality of openings (for example, two, three, four, or more openings can be positioned on a second (optionally, opposed side) of the nonconductive body. Optionally, the number of openings in the first plurality of openings can be equal to the number of openings in the second plurality of openings. In further aspects, it is contemplated that each side of the nonconductive body 55 can have a single opening 60 that is in fluid communication with the interior volume 58. In still further optional aspects, it is contemplated that the total area of the opening(s) on the first side of the nonconductive body can be equal or substantially equal to the total area of the opening(s) on the second side of the nonconductive body. Although discussed above as a single inner passageway 62, it is contemplated that the nonconductive body 55 can define a plurality of inner passageways, such as for example and without limitation, at least first and second inner passageways that extend between respective pairs of openings, with the openings of each pair being positioned on opposing sides of the nonconductive body.

In some aspects, the plurality of openings 60 can be positioned in an even distribution across the nonconductive body 55. In further aspects, the plurality of openings 60 can be concentrated at areas (e.g., clusters), optionally disposed at opposing ends of the nonconductive body 55. The openings 60 can be formed in a scaffold, a 3D printed construct, or a biosheet. Optionally, the openings 60 can be round (e.g., circular or oblong), rectangular slots, or any suitable shape. Optionally, each opening can have an area therethrough of at least 1 mm$^2$, at least 2 mm$^2$, from 2 mm$^2$ to 5 mm$^2$, at least 5 mm$^2$, or less than 5 mm$^2$. The nonconductive body 55 can have two openings 60, at least two openings, at least 4 openings, at least 6 openings, at least 10 openings, or fewer than 10 openings. Optionally, the openings 60 can collectively have an area that is at least 5% or at least 10% or no more than 20% or from 10% to 20% of the outer surface area of the nonconductive body 55. In further aspects, the inner passageway 62 can be defined by one or more bores through the nonconductive body 55 or by any other structure that provides electrical communication therethrough.

In further optional aspects, the nonconductive body 55 can define one or more pathways therethrough that can fill with fluid. For example, the nonconductive body 55 can comprise open cell foam that can fill with fluid. Accordingly, such a nonconductive body 55 can inhibit a portion of the electric fields therethrough, thereby directing a portion of the electric field around the outer circumference of the nonconductive body.

The resection cavity can optionally be within the brain of the patient. In further aspects, the resection cavity can be within the liver of the patient. In yet further aspects, the resection cavity can be within a lung of the patient. In yet still further aspects, it is contemplated that the resection cavity can be anywhere else (e.g., within any selected organ) in the body of the patient.

Figure 8:
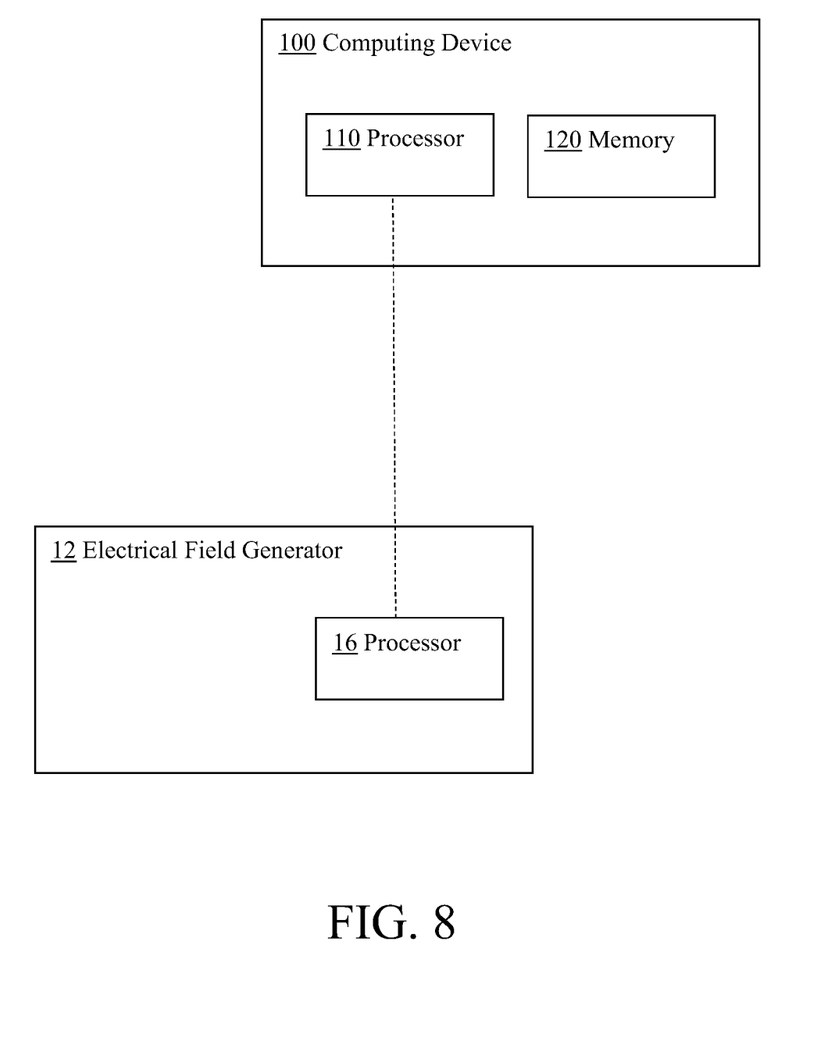
FIG. 8 is a schematic diagram depicting a computing device in communication with an electrical field generator as disclosed herein.

With reference to FIG. 8, in some exemplary aspects, a computing device 100 can be used to determine an optimal treatment plan in conjunction with usage of the disclosed nonconductive materials 54. In these aspects, the computing device 100 can comprise a processor 110 and a memory 120 storing processor-executable instructions that, when executed by the processor, cause the computing device to determine one or more features of the optimal treatment plan. Exemplary computing devices include, for example and without limitation, a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. In exemplary aspects, the processor 110 of the computing device 100 can be communicatively coupled (e.g., via wired or wireless connection) to the processor 16 of the electrical field generator 12 such that the computing device 100 can direct operation of the field generator 12 to achieve the optimal treatment plan. In these aspects, it is contemplated that the computing device 100 and the electrical field generator 12 can comprise respective transmitters, receivers, transceivers, and/or cables that are configured to permit such communication. Alternatively, in other aspects, the processor 16 of the electrical field generator 12 can be configured to determine an optimal treatment plan in the manner of the disclosed computing device 100.

In exemplary aspects, the computing device 100 can be configured to provide one or more of: optimal locations for transducer placement; optimal field strength; treatment duration; or field directional changes and timing thereof. The computing device 100 can receive geometry of at least a portion of the patient, including the resection cavity 52. For example, the computing device 100 can receive a medical image of the patient. In further aspects, the computing device 100 can receive a computer-generated model of the patient. In some optional aspects, the geometry of the nonconductive material 54 can be provided to the computing device 100. The computing device 100 can be configured to model an electric field between the transducers in order to optimize a treatment plan based, at least in part, on the pathway of the electric field circumventing the nonconductive material 54. The computing device 100 can further be configured to model the electric field based, at least in part, on the placement of the transducers and/or the geometry of the nonconductive material and/or the patient (e.g., geometry of the resection cavity). It is contemplated that the computing device 100 can optionally comprise a user interface (for example, and without limitation, a display and/or user input device) that is configured to allow an operator of the apparatus to enter information (e.g., one or more of the above-discussed parameters) that can be used to determine and/or execute the optimal treatment plan. Further details of a computing device and platform for providing the treatment plan are disclosed in U.S. patent application Publication Ser. No. 15/840,191, filed Dec. 12, 2017, which is hereby incorporated by reference herein in its entirety for all purposes.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A method comprising:

positioning a nonconductive material within a resection cavity that is adjacent to a target region;

positioning at least one first electrode and at least one second electrode relative to the tumor resection cavity so that electric fields between the at least one first electrode and the at least one second electrode travel through the target region; and generating tumor-treating electric fields between the at least one first electrode and the at least one second electrode.

Aspect 2: The method of aspect 1, wherein each of the at least one first electrode and the at least one second electrode comprises a plurality of electrodes arranged in respective electrode arrays.

Aspect 3: The method of aspect 1 or aspect 2, wherein the nonconductive material comprises at least one of a scaffold, a hydrogel, a film, or a 3D printed construct.

Aspect 4: The method of aspect 3, wherein the nonconductive material is a 3D printed construct, wherein the 3D printed construct comprises one of a hydrogel or a polyimide.

Aspect 5: The method of aspect 3, wherein the nonconductive material comprises a scaffold.

Aspect 6: The method of aspect 5, wherein the scaffold is one of a nanofibrous scaffold or a hybrid scaffold.

Aspect 7: The method of any one of aspects 5 or 6, wherein the scaffold comprises a natural polymer.

Aspect 8: The method of aspect 7, wherein the natural polymer comprises one or more of hyaluronic acid, fibrin, chitosan, gelatin, agarose or collagen.

Aspect 9: The method of any one of aspects 5 or 6, wherein the scaffold comprises a synthetic polymer.

Aspect 10: The method of aspect 9, wherein the synthetic polymer comprises Polyethylene Glycol (PEG), polypropylene fumarate (PPF), polyanhydride, polycaprolactone (PCL), polyphosphazene, polyether ether ketone (PEEK), polylactic acid (PLA), poly (glycolic acid) (PGA), or combinations thereof.

Aspect 11: The method of aspect 3, wherein the scaffold is a three-dimensional (3D) bi-layer scaffold comprising biological decellularized human amniotic membrane (AM) with viscoelastic electrospun nanofibrous silk fibroin (ESF).

Aspect 12: The method of any one of the preceding aspects, wherein the nonconductive material comprises a biosheet.

Aspect 13: The method of aspect 12, wherein the biosheet is a silicon sheet.

Aspect 14: The method of any one of the preceding aspects, wherein the nonconductive material comprises a chemotherapy agent.

Aspect 15: The method of any one of the preceding aspects, wherein the nonconductive material comprises an antibacterial agent.

Aspect 16: The method of any one of the preceding aspects, wherein the nonconductive material comprises an oil.

Aspect 17: The method of any one of the preceding aspects, wherein the nonconductive material defines an inner passageway that is configured to fill with fluid to conduct electric fields therethrough.

Aspect 18: The method of aspect 17, wherein the nonconductive material comprises a hollow body defining an inner volume and at least a first opening and a second opening that extend into the inner volume of the hollow body, wherein the inner passageway is defined at least in part by the first opening, the second opening, and the inner volume.

Aspect 19: The method of any one of the preceding aspects, further comprising: prior to positioning the nonconductive material within the resection cavity, resecting at least a portion of a tumor to form the resection cavity.

Aspect 20: The method of any one of the preceding aspects, wherein the resection cavity is within a brain.

Aspect 21: The method of any one of aspects 1-19, wherein the resection cavity is within a liver.

Aspect 22: The method of any one of aspects 1-19, wherein the resection cavity is within a lung.

Aspect 23: The method of any one of the preceding aspects, further comprising:
providing a port from the resection cavity through which the nonconductive material can travel; and
passing the nonconductive material through the port to remove the nonconductive material from the resection cavity after generating the tumor-treating electric fields between the at least one first electrode and the at least one second electrode.

Aspect 24: The method of aspect 23, further comprising passing the nonconductive material through the port to position the nonconductive material within the resection cavity.

Aspect 25: A system comprising:
at least one first electrode;
at least one second electrode;
a signal generator in electrical communication with each one of the at least one first electrode and the at least one second electrode, wherein the signal generator is configured to generate electric fields between the at least one first electrode and the at least one second electrode; and
a nonconductive material positioned between the at least one first electrode and the at least one second electrode.

Aspect 26: The system of aspect 25, wherein the nonconductive material defines an inner passageway that is configured to fill with fluid to conduct electric fields therethrough.

Aspect 27: The system of aspect 26, wherein the nonconductive material comprises a hollow body defining an inner volume and at least a first opening and a second opening that extend into the inner volume of the hollow body, wherein the inner passageway is defined at least in part by the first opening, the second opening, and the inner volume.

Aspect 28: The system of any one of aspects 25-27, wherein each of the at least one first electrode and the at least one second electrode comprises a plurality of electrodes arranged on respective electrode arrays.

Aspect 29: The system of any one of aspects 25-28, wherein the nonconductive material comprises at least one of a scaffold, a hydrogel, a film, or a 3D printed construct.

Aspect 30: The system of aspect 29, wherein the nonconductive material is a 3D printed construct, wherein the 3D printed construct comprises one of a hydrogel or a polyimide.

Aspect 31: The system of aspect 29, wherein the nonconductive material comprises a scaffold.

Aspect 32: The system of aspect 31, wherein the scaffold is one of a nanofibrous scaffold or a hybrid scaffold.

Aspect 33: The system of any one of aspects 31 or 32, wherein the scaffold comprises a natural polymer.

Aspect 34: The system of aspect 33, wherein the natural polymer comprises one or more of hyaluronic acid, fibrin, chitosan, gelatin, agarose or collagen.

Aspect 35: The system of any one of aspects 31 or 32, wherein the scaffold comprises a synthetic polymer.

Aspect 36: The system of aspect 35, wherein the synthetic polymer comprises Polyethylene Glycol (PEG), polypropylene fumarate (PPF), polyanhydride, polycaprolactone (PCL), polyphosphazene, polyether ether ketone (PEEK), polylactic acid (PLA), poly (glycolic acid) (PGA), or combinations thereof.

Aspect 37: The system of aspect 29, wherein the scaffold is a three-dimensional (3D) bi-layer scaffold comprising biological decellularized human amniotic membrane (AM) with viscoelastic electrospun nanofibrous silk fibroin (ESF).

Aspect 38: The system of any one of aspects 25-37, wherein the nonconductive material comprises a biosheet.

Aspect 39: The system of aspect 38, wherein the biosheet is a silicon sheet.

Aspect 40: The system of any one of aspects 25-39, wherein the nonconductive material comprises a chemotherapy agent.

Aspect 41: The system of any one of aspects 25-40, wherein the nonconductive material comprises an antibacterial agent.

Aspect 42: The system of any one of aspects 25-41, wherein the nonconductive material comprises an oil.

Aspect 43: The system of any one of aspects 27-42, wherein the first opening and the second opening are positioned on opposing sides of the hollow body.

Aspect 44: The system of any one of aspects 25-43, further comprising a computing device in communication with the signal generator.

Aspect 45: An apparatus comprising: a nonconductive body comprising a biocompatible material, wherein the nonconductive body is configured for receipt into a resection cavity, wherein the nonconductive body defines an inner passageway that is configured to fill with fluid to conduct electric fields therethrough.

Aspect 46: The apparatus of aspect 45, wherein the nonconductive body is hollow and defines an inner volume and at least a first opening and a second opening that extend into the inner volume of the nonconductive body, wherein the inner passageway is defined at least in part by the first opening, the second opening, and the inner volume.

Although the foregoing invention has been described in some detail by way of illustration and example for purposes of clarity of understanding, certain changes and modifications may be practiced within the scope of the appended claims.

What is claimed is:

1. A method comprising:
positioning a nonconductive material within a resection cavity that is adjacent to a target region, wherein the nonconductive material comprises a scaffold, wherein the scaffold comprises a natural polymer, wherein the scaffold is a three-dimensional (3D) bi-layer scaffold comprising biological decellularized human amniotic membrane (AM) with viscoelastic electrospun nanofibrous silk fibroin (ESF);
positioning at least one first electrode and at least one second electrode relative to the tumor resection cavity so that electric fields between the at least one first electrode and the at least one second electrode travel through the target region; and
generating tumor-treating electric fields between the at least one first electrode and the at least one second electrode.

2. The method of claim 1, wherein each of the at least one first electrode and the at least one second electrode comprises a plurality of electrodes arranged in respective electrode arrays.

3. The method of claim 1, wherein the scaffold further comprises a natural polymer, wherein the natural polymer comprises one or more of hyaluronic acid, fibrin, chitosan, gelatin, agarose or collagen.

4. The method of claim 1, wherein the scaffold further comprises a synthetic polymer, wherein the synthetic polymer comprises Polyethylene Glycol (PEG), polypropylene fumarate (PPF), polyanhydride, polycaprolactone (PCL), polyphosphazene, polyether ether ketone (PEEK), polylactic acid (PLA), poly (glycolic acid) (PGA), or combinations thereof.

5. The method of claim 1, wherein the nonconductive material comprises a biosheet.

6. The method of claim 1, wherein the nonconductive material comprises a chemotherapy agent.

7. The method of claim 1, wherein the nonconductive material comprises an antibacterial agent.

8. The method of claim 1, wherein the nonconductive material comprises an oil.

9. The method of claim 1, further comprising: prior to positioning the nonconductive material within the resection cavity, resecting at least a portion of a tumor to form the resection cavity.

10. The method of claim 1, wherein the resection cavity is within a brain.

11. The method of claim 1, wherein the resection cavity is within a liver.

12. The method of claim 1, wherein the resection cavity is within a lung.

13. A method comprising:
positioning a nonconductive material within a resection cavity that is adjacent to a target region;
positioning at least one first electrode and at least one second electrode relative to the tumor resection cavity so that electric fields between the at least one first electrode and the at least one second electrode travel through the target region; and
generating tumor-treating electric fields between the at least one first electrode and the at least one second electrode,
wherein the nonconductive material defines an inner passageway that is configured to fill with fluid to conduct electric fields therethrough.

14. The method of claim 13, wherein the nonconductive material comprises a hollow body defining an inner volume and at least a first opening and a second opening that extend into the inner volume of the hollow body, wherein the inner passageway is defined at least in part by the first opening, the second opening, and the inner volume.

15. A method comprising:
positioning a nonconductive material within a resection cavity that is adjacent to a target region;
positioning at least one first electrode and at least one second electrode relative to the tumor resection cavity so that electric fields between the at least one first electrode and the at least one second electrode travel through the target region;
generating tumor-treating electric fields between the at least one first electrode and the at least one second electrode;
providing a port from the resection cavity through which the nonconductive material can travel; and
passing the nonconductive material through the port to remove the nonconductive material from the resection cavity after generating the tumor-treating electric fields between the at least one first electrode and the at least one second electrode.

16. The method of claim 15, further comprising passing the nonconductive material through the port to position the nonconductive material within the resection cavity.

* * * * *